United States Patent [19]

Zaks et al.

[11] Patent Number: 5,316,927
[45] Date of Patent: May 31, 1994

[54] PRODUCTION OF MONOGLYCERIDES BY ENZYMATIC TRANSESTERIFICATION

[75] Inventors: Aleksey Zaks, Brookline; Akiva T. Gross, Newton, both of Mass.

[73] Assignee: Opta Food Ingredients, Inc., Bedford, Mass.

[21] Appl. No.: 942,476

[22] Filed: Sep. 9, 1992

Related U.S. Application Data

[63] Continuation of Ser. No. 809,844, Dec. 18, 1991, abandoned, which is a continuation of Ser. No. 253,110, Oct. 4, 1988, abandoned.

[51] Int. Cl.$^5$ .......................... C12P 7/64; C12P 7/62; C12N 9/20; C12N 11/14; C12N 11/16
[52] U.S. Cl. .................................. 435/134; 435/198; 435/135; 435/174; 435/176
[58] Field of Search ..................... 435/134, 198, 135

[56] References Cited

U.S. PATENT DOCUMENTS

| | | | |
|---|---|---|---|
| 4,275,081 | 6/1981 | Coleman et al. | 435/134 X |
| 4,735,900 | 4/1988 | Urata et al. | 435/134 |

FOREIGN PATENT DOCUMENTS

| | | |
|---|---|---|
| 0191217 | 8/1986 | European Pat. Off. . |
| .274798 | 7/1988 | European Pat. Off. . |
| 60-78587 | 5/1985 | Japan . |
| 60-234590 | 11/1985 | Japan ................................. 435/134 |
| 2188057 | 9/1987 | United Kingdom ............... 435/134 |

OTHER PUBLICATIONS

I. L. Gatfield, *Annals of the New York Academy of Science*, 434:569–572 (1984).
M. M. Hoq et al., *Agric. Biol. Chem.*, 49(2):335–342 (1985).
Hoq, M. M. et al., *Journal of the American Oil Chemists' Society*, 61(4):776–781 (1984).
Y. Tsujisaka et al., *Biochim. Biophys. Acta*, 489(3):415–422 (1977).
R. A. Wisdom et al., *Enzyme Microb. Technol.*, 6(10):443–446 (1984).
F. Bozoglu et al., *J. Agric. Food Chem.*, 23:2–6 (1984).
R. G. Jensen et al., *Journal of the American Oil Chemists' Society*, 55:422–427 (1978).
N. O. V. Sonntag, *Journal of the American Oil Chemists' Society*, 56:751A–754A (1979).
G. Lazar et al., In: *World Conference of Emerging Technol. Fats, Oils, Ind.*, (1985), pp. 346–354.
B. Borgstrom, *Biochim. Biophys. Acta*, 84:228–250 (1964).
Chemical Abstracts 109:5280v (1988).
Chemical Abstracts 103:100832m (1985).
Chemical Abstracts 103:121766h (1985).
Chemical Abstracts 104:48227x.
Chemical Abstracts 100:31332x.
Chemical Abstracts 100:81857t.
Chemical Abstracts 105:113635r.
Chemical Abstracts 101:187432m.

*Primary Examiner*—Douglas W. Robinson
*Assistant Examiner*—Jon P. Weber
*Attorney, Agent, or Firm*—Hamilton, Brook, Smith & Reynolds

[57] ABSTRACT

A process for the production of high purity monoglycerides by lipase-catalyzed transesterification, and the products of the reaction, are described. In the method of the present invention, oils or pure triglycerides are combined with alcohol, a small amount of water and a lipase. The reaction proceeds under mild conditions, and produces high yields of $\beta$-monoglyceride product.

9 Claims, No Drawings

PRODUCTION OF MONOGLYCERIDES BY ENZYMATIC TRANSESTERIFICATION

This is a continuation of copending application Ser. No. 07/809,844, filed on Dec. 18, 1991 now abandoned, which is a continuation of copending application Ser. No. 07/253,110 filed on Oct. 4, 1988 now abandoned.

BACKGROUND

Monoglycerides represent an important class of surfactants which are widely used as additives in the food industry. Being excellent emulsifiers, monoglycerides help to distribute and stabilize droplets of two immiscible liquids in one another, which improves the texture, homogeneity, consistency and overall quality of these products. Useful properties of monoglycerides, such as a high tendency to form complexes with starch, an ability to modify the crystal structure of foods, and significant aerating and stabilizing effects make them indispensable in the production of baked goods, cake mixtures, salad dressings, frozen deserts and other processed foods. Due to their high surface activity, monoglycerides also have various applications in the pharmaceutical and plastics industries.

Currently, monoglycerides are produced commercially by glycerolysis of fats. In this process, the fatty acid groups are transferred from triglycerides to the available hydroxyl groups of the glycerol to give a mixture of mono-, di- and triglycerides. The monoglycerides must then be isolated by molecular distillation, at high vacuum. The major drawback of the chemical process described above are the low product yield and the high cost of molecular distillation. A large fraction of the yield losses is caused by thermal degradation at the high temperatures used during the reaction and purification.

Another method of producing monoglycerides is by enzymatic transformations. Several reaction pathways for obtaining fatty acid glycerides can be used: the esterification of glycerol with fatty acid; the glycerolysis of triglycerides; and partial hydrolysis of triglycerides. I. L. Gatfield in *Ann. N.Y. Acad. Sci.*, 434:569–72 (1984). Japanese Patent No. 118,094 describes the production of monoglycerides by a lipase-catalyzed transesterification reaction between the alkyl ester of a fatty acid, in this case methyl oleate, and glycerol. The preparation of various types of glyceride esters using lipase is described by G. Lazar in *Fette Seifen, Anstrichm.*, 87(10):394–400 (1985). The lipase-catalyzed synthesis of glycerides from free fatty acids and glycerol is described by M. K. Tahoun et al., *Microbios. Letts.*, 28(111–112):133–139 (1985); M. M. Hoq et al., *Agric. Biol. Chem.*, 49(2):335–42 (1985); T. Yamane et al., *Ann. N.Y. Acad. Sci.*, 434:558–568 (1984); M. Pina and J. Graille, *Bull. Tech./Gattefosse Rep.*, 76:34–36 (1984); M. M. Hoq et al., *J. Am. Oil Chem. Soc.*, 61(4):776–781 (1984); N. Muthukumaran and S. C. Dhar, *Leather Sci.*, 30(3):97–100 (1983); Y. Tsujisaka et al., *Biochem. Biophys. Acta.* 489(3):415–522 (1977); and R. Bacaloglu et al., *Rev. Roum. Biochem.*, 22(3):177–181 (1985).

There are several limitations to the previous processes, including, the need for an excess of glycerol, a low degree of conversion, and complex purification procedures.

SUMMARY OF THE INVENTION

The invention relates to a process for preparing monoglycerides by the lipase-catalyzed transesterification of triglycerides in an alcohol medium. In the present process, a selected enzyme is added to a solution or an emulsion of triglycerides in alcohol (e.g., ethanol) containing a certain amount of water. A selected lipase is added to the reaction medium and a suspension is formed, as lipases are insoluble in most organic solvents. The suspension is agitated until the reaction is complete, after which the enzyme is removed, and the monoglyceride products are separated from the reaction mixture. The yield of isolated $\beta$-monoglycerides in the present process is about 90%.

The present process affords high yields of monoglycerides having a unique structure, namely monoglycerides acylated in the $\beta$-position. On the contrary, traditional chemical methods result in the production of only $\alpha$-acylated monoglycerides.

The present process has several other advantages, including low by-product formation, mild reaction conditions, easy product separation, and formation of fatty acid esters as a second major product of the reaction. These fatty acid esters are valuable by-products and can be used either directly in the cosmetics industry or as a starting material in the synthesis of various products, such as fatty alcohols, amines, etc. The operational stability of the lipase biocatalyst is quite high, and the biocatalyst can be easily reused. The reaction can be carried out at ambient or slightly elevated temperatures. In addition, the present process, in contrast to prior ones, requires neither prior hydrogenation of highly unsaturated triglycerides, nor high temperature distillation of the product.

DETAILED DESCRIPTION OF THE INVENTION

In nature, lipases catalyze the hydrolysis of fats and oils. The following scheme shows the complete hydrolysis of a triglyceride to glycerol and fatty acids:

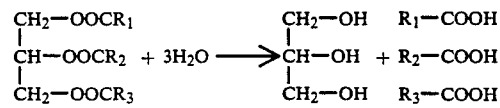

wherein $R_1$, $R_2$ and $R_3$ represent the hydrocarbon backbone chains of fatty acids. In addition to the hydrolysis reaction, lipases can catalyze transesterification reactions between triglycerides and a variety of alcohols.

The process of the invention utilizes selected lipases to catalyze the partial transesterification of triglycerides to form monoglycerides in high yields while minimizing the formation of glycerol and diglycerides. The monoglycerides formed are acylated predominantly in the $\beta$-position. Fatty acid esters are a second major product of the reaction.

Triglycerides from any source can be used in the present process. Both saturated and unsaturated triglycerides can be used, for example, soybean oil or corn oil may be used as the triglyceride source.

Different lipases obtained from a variety of sources, including mammals, yeast, mold and bacteria can be employed as catalysts in the present process. Lipases used in the present process should exhibit high operational stability (e.g., can be reused without loss of bioactivity for at least 72 hours), be active in a near-anhydrous organic medium (e.g., the amount of water is less than 5%), and efficienty catalyze the transestification reaction between an alcohol and a triglyceride. The term "efficiently catalyze" means that a yield of about 90% of monoglyceride is obtained when the lipase is used. Lipases which have been successfully used for the present process are lipases derived from *Pseudomonas fluorscens*, and porcine pancrease. In the present process, it was found that at least 90% activity of *Pseudomonas fluorescens* lipase or porcine pancreatic lipase was present after continuous use for at least 72 hours.

The present reaction is carried out in an alcohol medium. The alcohol serves also as a reactant. Primary or secondary alkyl alcohols can be used, including, for example, methanol, ethanol, propanol, isopropanol, butanol, isobutanol, pentanol, pentanediol, isopentanol and hexanol. Mixtures of alcohols (e.g., ethanol/butanol) can also be used. Ethanol is a preferred alcohol. When ethanol is used, monoglycerides and ethyl esters of fatty acids are produced in yields of about 90%. The regiospecificity of the *Pseudomonas fluorescens* lipase and porcine pancreatic lipase in the present process is such that up to about 95% of monoglycerides are acylated in the $\beta$-position.

The presence of a small amount of water in the alcohol accelerates the reaction and affects the distribution of the products. The preferred amount of water in the present process is from about 1 to about 5% by volume of the alcohol. About 3% water by volume is particularly preferred. For example, the reaction rate in an alcohol medium containing about 3% water, when lower alcohols (i.e., 4 carbon atoms or less) are used, is at least three times higher than the reaction rate in the presence of 1% water. Lower yields of monoglycerides are obtained when no water is used. At higher water concentrations (e.g., >5% by volume), the hydrolysis reaction starts to compete with the transesterification reaction, resulting in the formation of undesirable free fatty acids.

In the present process, the triglyceride is combined with an alcohol containing a small amount of water. The reaction is started by the addition of lipase to the reaction mixture. Lipase can be in the form of a dry powder, or immobilized on a support, such as silica or diatomaceous earth, or on a microcarrier, such as polystyrene or dextran beads. The reaction can be carried out in any appropriate reaction vessel, including a tank reactor, a packed column or a membrane bioreactor.

If a tank reactor is used, it is necessary to provide sufficient agitation in order to eliminate diffusional limitations. Agitation can be achieved by shaking or stirring; for example, stirring with a magnetic stirrer or an impeller blade, can be used. Agitation speeds should be sufficient to form and maintain the suspension.

The temperature of the reaction mixture may range from about 20° C. to about 60° C. A preferred temperature range is from about 25° C. to about 45° C.

The reaction should be allowed to proceed for a time sufficient to convert most of the triglyceride to monoglyceride. Reaction times can vary from about 2 to about 20 hours depending on the amount of the catalyst. The course of the reaction can be monitored by chromatography (e.g., gas or thin layer chromatography). After the reaction is complete, lipase is removed, either by centrifugation or filtration. The reaction products, ethyl esters of the fatty acids, free fatty acids and monoglycerides, are then separated. Separation can be accomplished by crystallization, membrane filtration or chromatography. The yield of $\beta$-monoglycerides using this process can be up to about 90%.

Additives can, optionally, be added to the enzyme preparation. Calcium ions, for example, can be used to improve the stability and activity of the enzyme.

The invention is further illustrated by the following exemplification:

EXEMPLIFICATION

Materials

Lipases (EC 3.1.1.3) were obtained from the following suppliers: porcine pancreatic lipase from Sigma Chemical Co. (St. Louis, Mo.) and *Pseudomonas fluorescens* from Amano International Enzyme Co. (Troy, Va.). The porcine pancreatic lipase had a specific activity of 110 IU/mg solids and *Pseudomonas fluorescens* lipase had a specific activity of 30 IU/mg solids. Monoolein, diolein, triolein, soybean and corn oil were also purchased from Sigma. All solvents used in this work were of analytical grade and were obtained from Aldrich Chemical Co. (Milwaukee, Wis.).

Methods

The activity of the lipase in the hydrolysis reaction was determined potentiometrically (Radio-meter RTS-812 recording pH-stat system) using either tributyrin or corn oil as substrates. In this process, 10 mL of an 0.1 g/mL aqueous solution of a substrate was placed in the cuvette of a pH-stat, and the pH was adjusted to 7.0. A lipase sample was then added, and the acid which was liberated as a result of enzymatic hydrolysis was automatically titrated with 0.5M NaOH.

All products of enzymatic conversions were assayed by gas chromatography (GC) using 12-m fused silica capillary column (S.G.E. Australia). Nitrogen was used as a carrier gas (5 mL/min), and the detector and injector port temperatures were 350° C. The starting temperature of the column was 100° C., and after the injection it increased to 350° C. at 20° C./min. The retention times were 7.35 minutes for monoolein; 11.3 minutes for diolein, and 19.8 minutes for triolein. For precise quantitative analysis, prior to the injection the reaction mixture was silylated with hexamethyldisilazane following the standard procedure described by Sweeley et al. in *J. Am. Chem. Soc.*, 85:2495-2507 (1963).

In addition to GC, the course of the reactions and the purity of all products were follwed by thin-layer chromatography (TLC) using Whatman K6 silica gel sheets. A mixture of petroleum ether (b.p. 30°-60° C.), ether and acetic acid in a ratio of 90:10:1 was used as an eluting buffer. The spots were developed by spraying with 50% $H_2SO_4$, followed by 10 minutes of heating at 180° C.

Enzymatically prepared monoglycerides were separated either by flash silica gel chromatography or by crystallization. For flash silica gel chromatography, the solvent was evaporated under reduced pressure, and 5 g of the reaction products were applied on a column (diameter: 2.5 inches; length: 2.0 inches) packed with silica gel and equilibrated with a petroleum ether:ether mixture in a ratio of 9:1. The byproducts were eluted with the above mixture at a flow rate of about 70 ml/min. Monoglycerides were eluted in the same manner using anhydrous diethyl ether as elutant.

The acidity of silica gel stimulates the migration of the acyl moiety from the $\beta$-position to the more stable α-position of monoglyceride. Consequently, chromatographic separation results in the formation of a mixture of monoglycerides acylated in the α or β position. If exclusively β-monoglycerides are required, the products should be separated by crystallization using the following procedure: After the completion of the reaction (e.g., transesterification between triolein and ethanol), the enzyme was separated by centrifugation and the solvent evaporated under reduced pressure. The resultant oily liquid (5 g) containing monoglycerides, free fatty acids and their alkyl esters was dissolved in 30 ml hexane at room temperature. The solution was cooled to −18° C. and left at this temperature for 1 hour. White crystals formed, were separated by filtration and washed with hexane (at −18° C.). β-Monoacylated glycerol of 97% purity was obtained using this method.

EXAMPLE 1

Triolein (4.5 g) was placed into a round-bottom flask containing 45 mL of 97% (v/v) ethanol (3% water). One g of *Pseudomonas fluorescens* lipase in the form of a dry powder was added to the flask. The formed suspension was agitated on an orbit shaker at 400 rpm at a temperature of 20° C. The course of the reaction was monitored by GC, following the disappearance of the triolein and the appearance of the products (i.e., monoolein and ethyl ester of oleic acid). After 20 hours, no starting material was observed in the reaction mixture. As determined by GC and TLC, the major products of the reaction wee monoolein and ethyl ester of oleic acid. The reaction was stopped by removing the enzyme, which was done by filtering the reaction mixture through a sintered glass filter. The solvent was then evaporated under vacuum using a rotary evaporator, and the monoglyceride product was purified on a silica gel column. As a result, 1.5 g of monoolein was produced. The purity of the product was at least 95%, as determined by GC and TLC.

EXAMPLE 2

Various oils can also be used as starting material for the production of monoglycerides. The procedure described in Example 1 was followed, except that 4.5 g of soybean oil was substituted for triolein. As a result, 1.4 g of 95% pure monoglycerides were produced.

EXAMPLE 3

The procedure described in Example 1 was followed, except that 97% (v/v) butyl alcohol (3% water) substituted for 97% ethanol. As a result, 1.5 g of 95% pure monoolein were produced.

EXAMPLE 4

Five grams of tripalmitin were placed in a flask containing 50 ml of 97% (v/v) butanol (3% water). One gram of *Pseudomonas fluorescens* lipase was added, and the suspension was stirred on an orbit shaker at 400 rpm at 45° C. for 30 hr. The product was purified by crystallization from hexane. As a result, 1.2 g of monopalmitate (97% purity) were obtained.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of preparing β-acrylated monoglycerides by enzymatic transesterification of triglycerides in an alcohol medium, comprising the steps of:
    a) combining a primary or secondary alkyl alcohol, as the medium, selected from the group consisting of methanol, ethanol, propanol, isopropanol, butanol, isobutanol, pentanol, isopentanol and hexanol and mixtures thereof, with triglycerides and from about 1 to about 5% by volume water;
    b) adding a 1,3-regiospecific lipase to the combination formed in (a), whereby the lipase catalyzes transesterification of the triglycerides but avoids acyl migration of fatty acid moieties from the 2-position to the 1-position on said triglycerides;
    c) maintaining the combination obtained in (b) under agitating conditions and at a temperature from about 20° C. to about 60° C. sufficient for transesterification to occur between the hydroxyl groups of the alcohol and two of the fatty acid groups of the triglyceride, whereby about 90% by weight of the triglycerides are converted to β-acylated monoglycerides; and
    d) terminating the reaction and separating the monoglyceride product from the fatty acid ester by-product.

2. A method of claim 1, wherein the selected lipase catalyst is derived from *Pseudomonas fluorescens*.

3. A method of claim 1 wherein the selected lipase catalyst is porcine pancreatic lipase.

4. A method of claim 3 wherein the lipase is immobilized on a carrier.

5. A method of claim 4 wherein the carrier comprises diatomaceous earth, silica or polystyrene beads.

6. The method of claim 1 wherein the reaction temperature is from about 25° C. to about 45° C.

7. The method of claim 1 wherein step (c) is maintained for about 2 to about 30 hours.

8. The method of claim 1 wherein 97% ethanol is used as the alcohol medium.

9. The method of claim 1 wherein the monoglyceride is separated by crystallization, membrane filtration or chromatography.

* * * * *